US010929487B1

(12) United States Patent
Kamvar et al.

(10) Patent No.: US 10,929,487 B1
(45) Date of Patent: *Feb. 23, 2021

(54) CUSTOMIZATION OF SEARCH RESULTS FOR SEARCH QUERIES RECEIVED FROM THIRD PARTY SITES

(71) Applicant: Google LLC, Mountain View, CA (US)

(72) Inventors: Sepandar D. Kamvar, San Francisco, CA (US); Taher H. Haveliwala, Fremont, CA (US); Glen M. Jeh, San Francisco, CA (US)

(73) Assignee: Google LLC, Mountain View, CA (US)

( * ) Notice: Subject to any disclaimer, the term of this patent is extended or adjusted under 35 U.S.C. 154(b) by 286 days.

This patent is subject to a terminal disclaimer.

(21) Appl. No.: 15/902,202

(22) Filed: Feb. 22, 2018

Related U.S. Application Data

(63) Continuation of application No. 14/875,771, filed on Oct. 6, 2015, now Pat. No. 9,940,398, which is a
(Continued)

(51) Int. Cl.
*G06F 16/9535* (2019.01)
*A61K 48/00* (2006.01)
(Continued)

(52) U.S. Cl.
CPC ......... *G06F 16/9535* (2019.01); *A61K 48/00* (2013.01); *G06F 16/248* (2019.01);
(Continued)

(58) Field of Classification Search
None
See application file for complete search history.

(56) References Cited

U.S. PATENT DOCUMENTS 5,724,521 A 3/1998 Dedrick
5,724,567 A 3/1998 Rose et al.
(Continued)

FOREIGN PATENT DOCUMENTS

EP 1050830 11/2000
WO WO2001044992 6/2001
(Continued)

OTHER PUBLICATIONS

Aagarwal, et al., "A Framework for the Optimizing of the WWW Advertising,"International IFIP Working Conference on Electronic Commerce, 1998, Hamburg, Germany, published in Trends in Distributed Systems for Electronic Commerce, edited by W. Lamersdorf and M. Merz, Springer Verlag Lecture Notes in Computer Science, 1998, pp. 1-10, vol. 1402.
(Continued)

*Primary Examiner* — Kim T Nguyen
(74) *Attorney, Agent, or Firm* — Fish & Richardson P.C.

(57) ABSTRACT

A third party website provides a search interface to a general search engine. A site profile of the third party website describes various topics, keywords, or domains that are potentially relevant or of interest to users who access the third party website. The topics are associated with a topical directory, with domains associated with each topic; the domains in a given topic are given various weightings. When a search is submitted to the general search engine from the third party website via the search interface, the general search engine uses the site profile to customize the search results. The search results are customized by weighting the ranking of documents from websites associated with the topics in the site profile. The site profile can be manually or automatically constructed.

20 Claims, 5 Drawing Sheets

Related U.S. Application Data continuation of application No. 12/479,622, filed on Jun. 5, 2009, now Pat. No. 9,192,684, which is a continuation of application No. 10/869,492, filed on Jun. 15, 2004, now Pat. No. 7,565,630.

(51) Int. Cl.
*G06F 16/248* (2019.01)
*G06F 16/958* (2019.01)
*G06F 16/2455* (2019.01)
*G06F 16/2457* (2019.01)

(52) U.S. Cl.
CPC .... *G06F 16/2455* (2019.01); *G06F 16/24578* (2019.01); *G06F 16/986* (2019.01); *Y10S 707/99933* (2013.01); *Y10S 715/968* (2013.01)

(56) References Cited

U.S. PATENT DOCUMENTS

| | | |
|---|---|---|
| 5,754,938 A | 5/1998 | Herz et al. |
| 5,754,939 A | 5/1998 | Herz et al. |
| 5,809,242 A | 9/1998 | Shaw et al. |
| 5,887,133 A | 3/1999 | Brown et al. |
| 6,012,053 A | 1/2000 | Pant et al. |
| 6,112,202 A | 8/2000 | Kleinberg |
| 6,134,532 A | 10/2000 | Lazarus et al. |
| 6,137,911 A | 10/2000 | Zhilyaev |
| 6,138,113 A | 10/2000 | Dean et al. |
| 6,154,737 A | 11/2000 | Inaba et al. |
| 6,285,999 B1 | 9/2001 | Page |
| 6,289,342 B1 | 9/2001 | Lawrence et al. |
| 6,308,202 B1 | 10/2001 | Cohn et al. |
| 6,327,574 B1 | 12/2001 | Kramer et al. |
| 6,327,590 B1 | 12/2001 | Chidlovskii et al. |
| 6,349,307 B1 | 2/2002 | Chen |
| 6,356,898 B2 | 3/2002 | Cohen et al. |
| 6,360,221 B1 | 3/2002 | Gough et al. |
| 6,366,298 B1 | 4/2002 | Haitsuka et al. |
| 6,370,527 B1 | 4/2002 | Singhal |
| 6,385,592 B1 | 5/2002 | Angles et al. |
| 6,385,619 B1 | 5/2002 | Eichstaedt et al. |
| 6,446,061 B1 | 9/2002 | Doerre et al. |
| 6,449,657 B2 | 9/2002 | Stanbach, Jr. et al. |
| 6,560,600 B1 | 5/2003 | Broder |
| 6,567,800 B1 | 5/2003 | Barrera et al. |
| 6,584,468 B1 | 6/2003 | Gabriel et al. |
| 6,601,061 B1 | 7/2003 | Holt et al. |
| 6,654,725 B1 | 11/2003 | Langheinrich et al. |
| 6,665,656 B1 | 12/2003 | Carter |
| 6,665,837 B1 | 12/2003 | Dean et al. |
| 6,665,838 B1 | 12/2003 | Brown et al. |
| 6,681,223 B1 | 1/2004 | Sundaresan |
| 6,684,205 B1 | 1/2004 | Modha et al. |
| 6,772,200 B1 | 8/2004 | Bakshi et al. |
| 6,799,176 B1 | 9/2004 | Page |
| 6,848,077 B1 | 1/2005 | McBrearty et al. |
| 6,859,802 B1 | 2/2005 | Rui |
| 6,871,202 B2 | 3/2005 | Broder |
| 6,912,505 B2 | 6/2005 | Linden et al. |
| 6,922,685 B2 | 7/2005 | Greene et al. |
| 6,980,962 B1* | 12/2005 | Arganbright ........... G06Q 30/02 705/14.23 |
| 7,050,617 B2 | 5/2006 | Kiefer et al. |
| 7,100,111 B2* | 8/2006 | McElfresh ............ G06Q 30/02 715/207 |
| 7,206,778 B2* | 4/2007 | Bode .................. G06F 16/3338 |
| 7,240,049 B2 | 7/2007 | Kapur |
| 7,250,095 B2 | 7/2007 | Black et al. |
| 7,346,605 B1* | 3/2008 | Hepworth ............ G06Q 10/00 |
| 7,565,630 B1 | 7/2009 | Kamvar et al. |
| 7,778,884 B2* | 8/2010 | Bamborough ..... G06Q 30/0222 705/14.36 |
| 8,036,990 B1 | 10/2011 | Mir et al. |
| 8,239,272 B2* | 8/2012 | Bamborough ......... G06Q 30/02 705/26.1 |
| 2002/0024532 A1 | 2/2002 | Fables et al. |
| 2002/0038348 A1 | 3/2002 | Malone et al. |
| 2002/0078045 A1 | 6/2002 | Dutta |
| 2002/0099685 A1 | 7/2002 | Takano et al. |
| 2002/0120619 A1 | 8/2002 | Marso et al. |
| 2002/0123912 A1 | 9/2002 | Subramanian et al. |
| 2002/0198882 A1 | 12/2002 | Linden et al. |
| 2003/0037041 A1 | 2/2003 | Hertz |
| 2003/0065774 A1 | 4/2003 | Steiner et al. |
| 2003/0088562 A1 | 5/2003 | Dillon et al. |
| 2003/0191737 A1 | 10/2003 | Steele et al. |
| 2003/0204501 A1 | 10/2003 | Moon |
| 2003/0204502 A1 | 10/2003 | Tomlin et al. |
| 2003/0208478 A1 | 11/2003 | Harvey |
| 2003/0233345 A1 | 12/2003 | Perisic et al. |
| 2004/0024752 A1 | 2/2004 | Manber et al. |
| 2004/0044571 A1 | 3/2004 | Bronnimann |
| 2004/0073485 A1 | 4/2004 | Liu et al. |
| 2004/0111412 A1 | 6/2004 | Broder |
| 2004/0249709 A1 | 12/2004 | Donovan et al. |
| 2005/0080771 A1 | 4/2005 | Fish |
| 2005/0091111 A1 | 4/2005 | Green et al. |
| 2005/0114306 A1* | 5/2005 | Shu ..................... G06F 16/9535 |
| 2005/0216434 A1 | 9/2005 | Haveliwala et al. |
| 2006/0026147 A1 | 2/2006 | Cone et al. |
| 2007/0239680 A1 | 10/2007 | Oztekin et al. |
| 2008/0065611 A1* | 3/2008 | Hepworth ............. G06F 16/951 |

FOREIGN PATENT DOCUMENTS

| | | |
|---|---|---|
| WO | WO2001063472 | 8/2001 |
| WO | WO2003107127 | 12/2003 |

OTHER PUBLICATIONS

Barroso, et al., "Web Search for a Planet: The Google Cluster Architecture," IEEE Micro, Mar.-Apr. 2003, pp. 22-28.
Bothe, et al., "On Current Technology for Information Filtering and User Profiling in Agent-Based Systems, Part I: A Perspective", CWI, Centre for Mathematics and Computer Science, Jan. 2000, pp. 1-12.
Brin, et al. "The Anatomy of a Large-Scale Hypertextual Web Search Engine," Computer Networks and ISDN Systems, Apr. 1998, pp. 107-117, vol. 30, No. 1-7.
Carr, "Using Interaction Object Graphs to Specify Graphical Widgets," Dept. of Computer Science, Univ. of Maryland, Sep. 1994.
Cho et al., "Efficient Crawling Through URL Ordering," Compute: Networks and ISDN Systems, Apr. 1998, pj>. 161-171, vol. 30, No. 1-7.
CNN.com Screenshots from archive.org dated Jan. 29, 2003.
Dumais, et al., "Stuff I've Seen: A System for Personal Information Retrieval and Re-Use", SIGIR '03, Jul. 28-Aug. 1, 2003, pp. I-8.
Geiger et al., "Asymptotic Model Selection for Directed Networks with Hidden Variables," May 1996, Technical Report MSR -TR -96-07, Microsoft Research, Advanced Technology Division.
Haveliwala "Topic-Sensitive PageRank" International World Wide Web Conference Proceedings of the 11th International Conference on World Wide Web, Honolulu, Hawaii Session: .Link analysis pp. 517-526 Published 2002.
Haveliwala "Topic-Sensitive PageRank. A Context-Sensitive Ranking Algorithm for Web Search," IEEE Transactions of Knowledge and Data Engineering, 2003.
Haveliwala et al., "An Analytical Comparison of Approaches to Personalizing PageRank," Stanford University Technical Report, 2003-35, Jun. 20, 2003.
Heckerman et al., "Learning Bayesian Networks: The Combination of Knowledge and Statistical Data," Microsoft Research Advanced Technology Division, Mar. 1994, pp. 1-53.
International Search Report re International Application No. PCT/US2004/026631, International Filing Date Aug. 13, 2004.
International Search Report re International Application No. PCT/US2005/025081 , dated Dec. 2, 2005.
Jeh, G., Widom, J., "Scaling personalized web search", In Proceedings of the 12th international 26 Conference on World Wide Web (Budapest, Hungary, May 20-24, 2003). WWW '03. ACM Press, New York, NY, pp. 271-279.

(56) References Cited

OTHER PUBLICATIONS

Jordan et al. "Hidden Markov Decision Trees, "Center for Biological and Computational Learning Massachusetts Institute of Technology and Department of Computer Science, University of Toronto.
Kohda et al., "Ubiquitous Advertising on the WWW: Merging Advertisement on the Browser," Fifth International World Wide Conference, May 6-10, 1996, pp. 1-9, Paris, France.
Langheinrich, et al., "Unintrusive Customization Techniques for Web Advertising," Computer Networks, 1999, pp. 1259-1272, vol. 31, No. 11-16.
Lawley, Elizabeth Lane, "Mamamusings", "MSR Presentations to Search Champs", http://mamamusings.netJarchives/2004/10/05/msr_presentations_to_searchchamps, Oct. 5, 2004, p. 1 of 1.
Liao et al., "Browsing Unix Directories with Dynamic Queries: An Evaluation of Three 16 Information Display Techniques," Technical Report CAR-TR-605 CS-TR 2841, Dept. of Computer Science, Univ. of Maryland, Feb. 1992.
Marais, J., Bhara. K., "Support cooperative and personal surfing with a desktop assistant" Proceedings of ACM U1ST'97, Oct. 1997.
Matthews, "Automating Ad Intelligence," Silicon Valley, Jul. 24, 2000, [online] Retrieved from the Internet<URL:http:siliconvalley.internet.com1news/artic le. php/3531 420651 >.
Meila et al., "Estimating Dependency Structure as a Hidden Variable," Massachusetts Institute of Technology, A.I. Memo No. 1648, C.B.C.L. Memo No. 165, Sep. 1998.
Meng et al., "Building Efficient and Effective Metasearch Engines," ACM Computing Surveys, Mar. 2002,~p. 48-49, vol. 34, No. 1.
Notice of Allowance issued in U.S. Appl. No. 13/549,645 dated Jun. 12, 2014, 17 pages.
Notice of Allowance issued in U.S. Appl. No. 14/875,771, dated Nov. 17, 2017, 8 pages.
Notice of Allowance issued in U.S. Appl. No. 12/479,622, dated Jul. 31, 2015, 10 pages.
Notice of Allowance issued in U.S. Appl. No. 12/479,622, dated May 29, 2015, 9 pages.
Office Action for U.S. Appl. No. 12/479,622 dated Feb. 15, 2012, 18 pages.
Office Action for U.S. Appl. No. 12/479,622 dated Jul. 25, 2011, 40 pages.
Office Action for U.S. Appl. No. 14/875,771, dated Aug. 23, 2017, 6 pages.
Office Action for U.S. Appl. No. 14/875,771, dated May 13, 2016, 13 pages.
Office Action for U.S. Appl. No. 14/875,771, dated Oct. 17, 2016, 13 pages.
Office Action issued in U.S. Appl. No. 13/549,645 dated Jan. 6, 2014, 22 pages.
Office Action issued in U.S. Appl. No. 13/549,645 dated May 8, 2013, 20 pages.
Office Action issued in U.S. Appl. No. 13/549,645 dated Oct. 2, 2013, 17 pages.
Office Action issued in U.S. Appl. No. 13/549,645 dated Oct. 3, 2012, 30 pages.
Osada et al., "Alpha Slider: Searching Textual Lists with Sliders," Dept. of Computer Science, Univ. of Maryland, Technical Report CS-TR-3078, Apr. 1993.
Pretschner et al., "Ontology Based Personalized Search," Proc. 11th IEEE Int. Conf. on Tools with Artificial Intelligence, Nov. 1999,k pp. 391-398, Chicago.
Rosenstein et al., "Recommending from Content: Preliminary Results from an E-Commerce Experiment," CHI 2000, published Apr. 16, 2000, The Hague, The Netherlands.
Sanchez, The Internet Digest "How to Get High Quality inbound Links", Aug. 2, 2003.
Weinburger, D., Microsoft Research, Joho the Blog, www.hyperorg.com, Oct. 2, 2003, pp. 1-3.

\* cited by examiner

CUSTOMIZATION OF SEARCH RESULTS FOR SEARCH QUERIES RECEIVED FROM THIRD PARTY SITES

CROSS-REFERENCE TO RELATED APPLICATIONS

This application is a continuation of U.S. application Ser. No. 14/875,771, filed on Oct. 6, 2015, which is a continuation of U.S. application Ser. No. 12/479,622, filed on Jun. 5, 2009, which is a continuation of U.S. application Ser. No. 10/869,492, filed on Jun. 15, 2004. The contents of each of the prior applications are incorporated by reference herein in their entirety.

TECHNICAL FIELD

This invention relates in general to online search engines, and in particular to customization of search results.

BACKGROUND

The current state of the art in online search engines is highly advanced in its ability to retrieve documents (e.g., web pages or portions thereof, images, audio files, video, multimedia, etc.) that are responsive to the terms of a query. Search engines today can quickly retrieve specific documents that match the terms of the query.

Web site operators often contract with a search engine provider to obtain an interface to the search engine on the operator's website. This allows users who are on the operator's website to perform a search of the entire internet from a search box on website. Conventionally, these searches will return the same results as if they were done directly from the web site of the search engine provider, in that they do not reflect any influence on the results in view of the contents or theme of the website, or the interests of the website operator.

For example, on a website that focuses on providing information about major league baseball, a general search on "giants" will typically return search results oriented to giants. However, the site operator would prefer to customize the search results to reflect the interests of users of the site, who presumably are interested in baseball. Thus, it would be preferable to the site operator if the generalized search instead returned results oriented towards the San Francisco Giants baseball team.

Similarly, using current search approaches, site operators of two different website, one of which is oriented towards sports, and another of which is oriented towards politics, will provides users of their respective sites exactly the same results a given query to a general search engine, for example, the query o the "drug testing in baseball." However, the first site operator would prefer that users obtain results about baseballs teams have implemented drug testing, while the latter site operator would prefer that users obtain results about legislation related to drug testing in sports. Thus, there is a need for providing a mechanism and methodology for customizing search results provided by a search engine in accordance with the interests of the site operators.

SUMMARY

The present invention provides allows a site operator specify a set of interests or topics which will influence the presentation of search results provided by general search engine in response to queries received the website of the operator. The present invention has multiple embodiments, including a system for providing a search engine, a methodology for processing a search query, and a site operator interface for the site operator to specify topics, and the degree of influence such topics have on search results.

For a site operator's perspective, the present invention provides a mechanism for customizing search results provided by a general search engine in response to queries received from the site operator's website. A general search engine is a search engine that performs a search on a generalized corpus such as the Internet and World Wide Web, and not limited to the contents of the site operator's website; a search essentially limited to the content of the site operator's site is called a site specific search. In one embodiment, the site operator provides a set of interests, for example as a set of topics or categories from a topical hierarchy or directory, which reflect the interests of the site operator or the expected users of the site operator's website. For example a site operator of a sports oriented website may choose topics such as "baseball," "football," "basketball", etc. as topics of interest.

In one embodiment, these topics are stored in a site profile associated with the site operator's website; alternatively the site profile can be stored at the search engine website. In another embodiment, the interests are encoded as parameters (e.g., topic IDs) that are stored with the code for the search query interface on the site operator's website, and passed to the general search engine as query string parameters, along with the search query terms, when a search query is entered in the search query box by a user. This approach may be described as runtime passing of the site operator's site profile.

In another embodiment, the interests can be extracted by keyword analysis of one or more web pages on the site operator's website to identify topical keywords; by link analysis of one or more web pages on the site operator's website or that link to the website; by analysis of site-to-site browsing of users who access the website; by analysis of prior search queries done on the site operator's website. In general, any attribute of the site operator's website can be used to define the interests of the site operator. Optionally, the site operator can also specify the degree to which the site profile influences the search results from a search.

The site operator provides one or more web pages on its website that include a search query interface to the general search engine, such as a search query box. A user visiting the website can input a search query to the general search engine via this search query interface. Depending on the implementation, the general search engine either retrieves the site profile (which contains the interests of the site operator) or receives the site profile in the query string parameters. In either case, the general search engine retrieves documents that are relevant to the query terms and presents these as search results. The search results are ranked according to the site operator's interests, as expressed in the site profile. Thus, the results that more relevant to the interests of the site operator will have a higher placement in the overall presentation of the search results.

In one embodiment, the ranking of search results operates to increase the relevance score of documents that are associated with topic directory. Each topic in the directory is associated with a group of documents (e.g., websites) that are deemed relevant to the topic. For each document (again, website), a weight (equivalently, a "boost") value is provided which indicates the degree of relevance of the site to the topic. All pages within a given site get that site's boost value. The boost value may be understood as a scaling factor that represents the relevance of the site to the topic. During query processing of a search query, the set of documents is returned, and each document is scored for its relevance to the query. If document is from one of the websites included in topics in the site operator's site profile, then the document's relevance score is adjusted by the weight, if any, of that website with respect to the topic. The adjustment may be, for example by multiplying the relevance score by the boost value, thereby scaling the relevance of the document to the query. Generally, only those documents which belong to sites listed in the directory will have a boosted relevance score, and other documents in the search results will not.

In one embodiment, as indicated above, the site operator can specify the degree of influence that the site profile has on the search results. This is done by using a customization control, which allows the site operator to specify a degree of influence from 0% to 100%. The input of the degree of influence can be textual (e.g., input of a number) or graphical. The ranking of the documents in accordance with their boosted relevance scores is then a function of the degree of influence, either from no influence (where the boost value has no effect on the relevance score) to complete influence, wherein boost value for a document is applied 100% to the document's relevance score, and any number of intermediate levels of application. The site operator can thus control the degree by which the site profile influences the ranking of documents in the search results by adjusting the position of the customization control.

A system embodiment includes a topic directory for providing topics (categories) to a site operator, a general search engine and index for searching indexed websites in response to a query received from a search query interface on the site operator's website, and in one embodiment, customization component for allowing the site operator to specify a degree of influence that the site profile will have determining the rankings of the search results to the search query. A site operator interface embodiment includes a topical directory, with various topics, and graphical controls (e.g., checkboxes) in which the site operator can select topics of interests, and, in one embodiment, a control that allows the site operator to adjust the search result ranking in accordance with his site profile.

The present invention is next described with respect to various figures and diagrams and technical information. The figures depict various embodiments of the present invention for purposes of illustration only. One skilled in the art will readily recognize from the following discussion that alternative embodiments of the illustrated and described structures, methods, and functions may be employed without departing from the principles of the invention.

DETAILED DESCRIPTION

Figure 1:
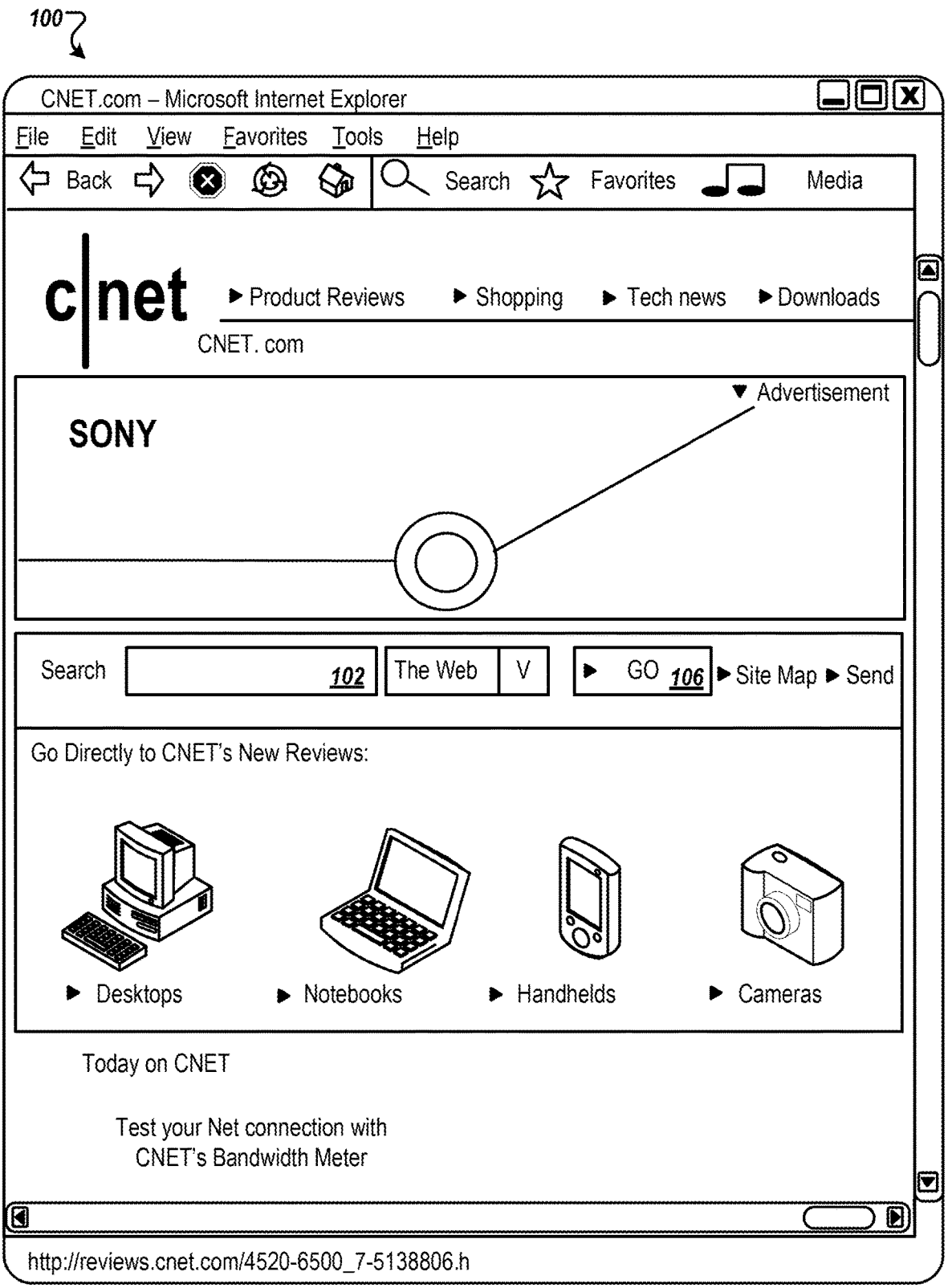
FIG. 1 illustrates a third party website of a site operator including search query interface to a general search engine.

Referring now to FIG. 1 there is shown a page 100 of site operator's website, including a search query interface to a general search engine. It is understood that the general search engine is operated at a different website provided by a search engine operator than the site operator's website. (A site operator's website will also be referred to herein as a "third party website," as it is a third party with respect to the general search engine operator.) The page 100 includes a query entry field 102 in which a user who is visiting the third party website can enter the terms of a search query. A search button 106 submits the query to the general search engine for processing.

Figure 2:
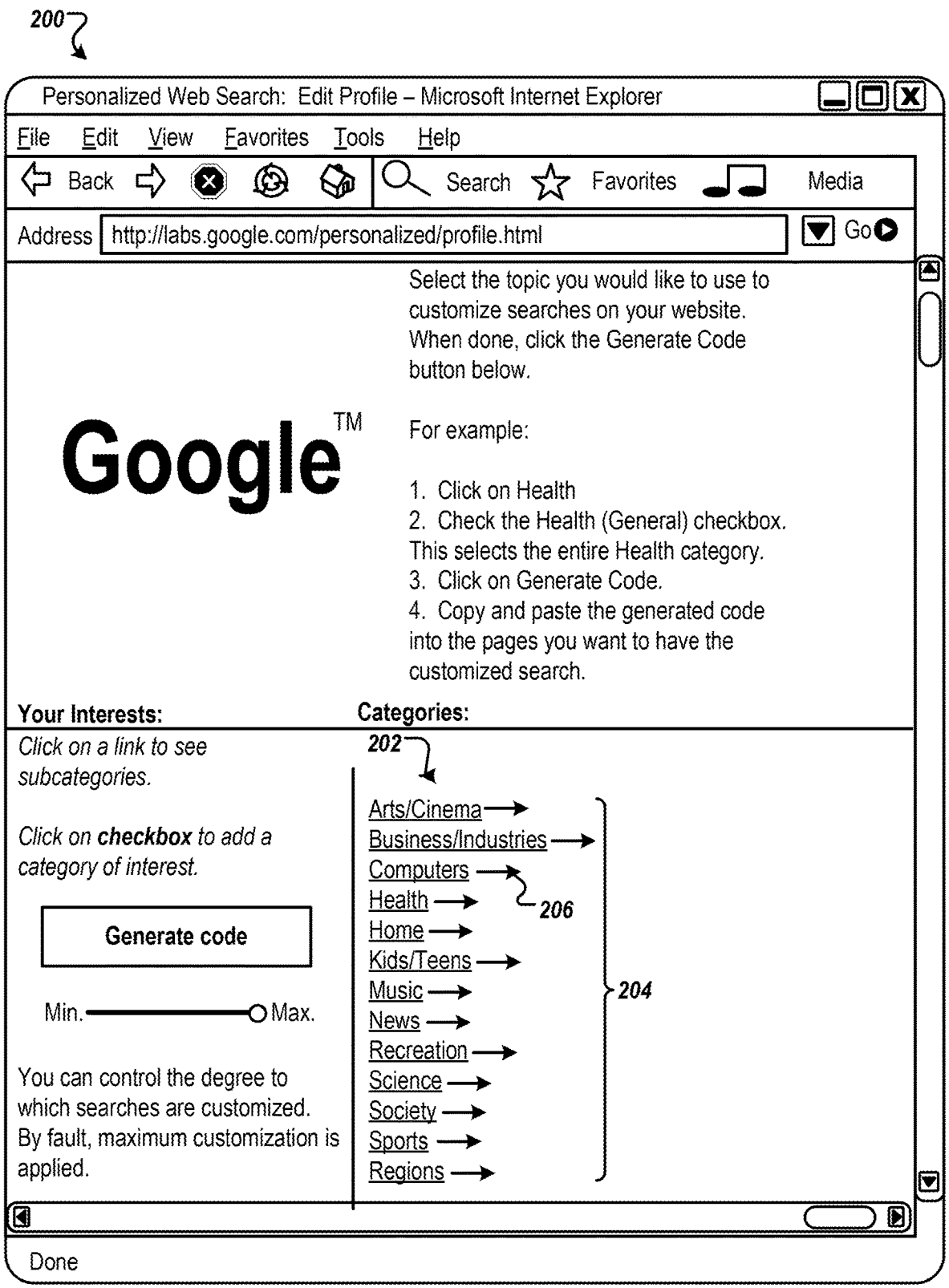
FIG. 2 illustrates a topical directory.

In one embodiment, the site operator defines a site profile via an interface provided by the general search engine operator. Referring to FIG. 2, there is shown a topical directory 202 that may be provided by general search engine operator to the third party site operator to define a site profile. The site operator uses the topical directory in order to identify the topics or interests to be used for customizing searches on the third party website. FIG. 2 shows the top level topics 204 of a topical directory 202. The topics in the directory can be, for example, the topics defined in the Open Directory Project, found at http://dmoz.org/ or can be some other topical directory. (The terms "topic" and "category" are interchangeable depending on the context, as are "subtopic" and "subcategory".) The top level topic links may have a set of subtopics, as indicated by the arrows 206. Clicking on a particular top level topic takes the site operator to a page associated with that topic's subtopics.

Figure 3:
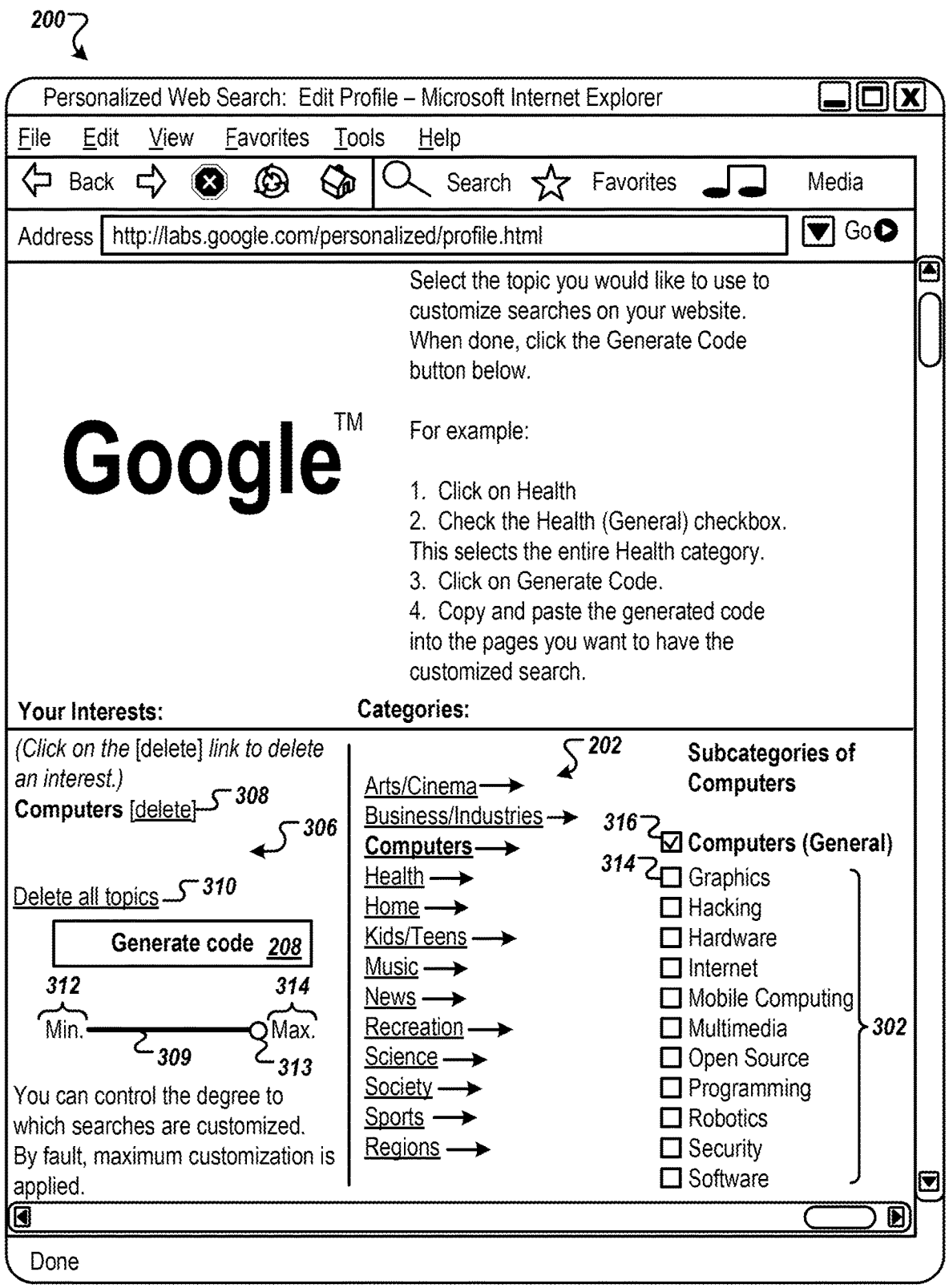
FIG. 3 further illustrates the topical directory, including various subtopics.

FIG. 3 illustrates the result of this step, where the site operator has clicked on the topic "Computers" on page 200. As shown in FIG. 3, the subtopics 302 of the topic "Computers" have been displayed in the right hand column. Next to each subtopic 302 is a checkbox 314. The site operator can select the checkbox 314 to indicate his interest in a specific subtopic. Alternatively, the site operator can select the checkbox 316 for the entire subtopic itself, "Computers (General)". This indicates that the site operator is interested in all of the subtopics of the topic "Computers". The set of topics selected by the site operator is called a site profile or a customization profile. On the left side of FIG. 3, after the site operator has selected one or more topics of interest, these topics are listed in the topics field 306 for the site operator's review. Next to each topic is a delete link 308 that allows the site operator to delete individual topics. The site operator can also delete all topics by selecting the "Delete all topics" link 310.

Figure 4:
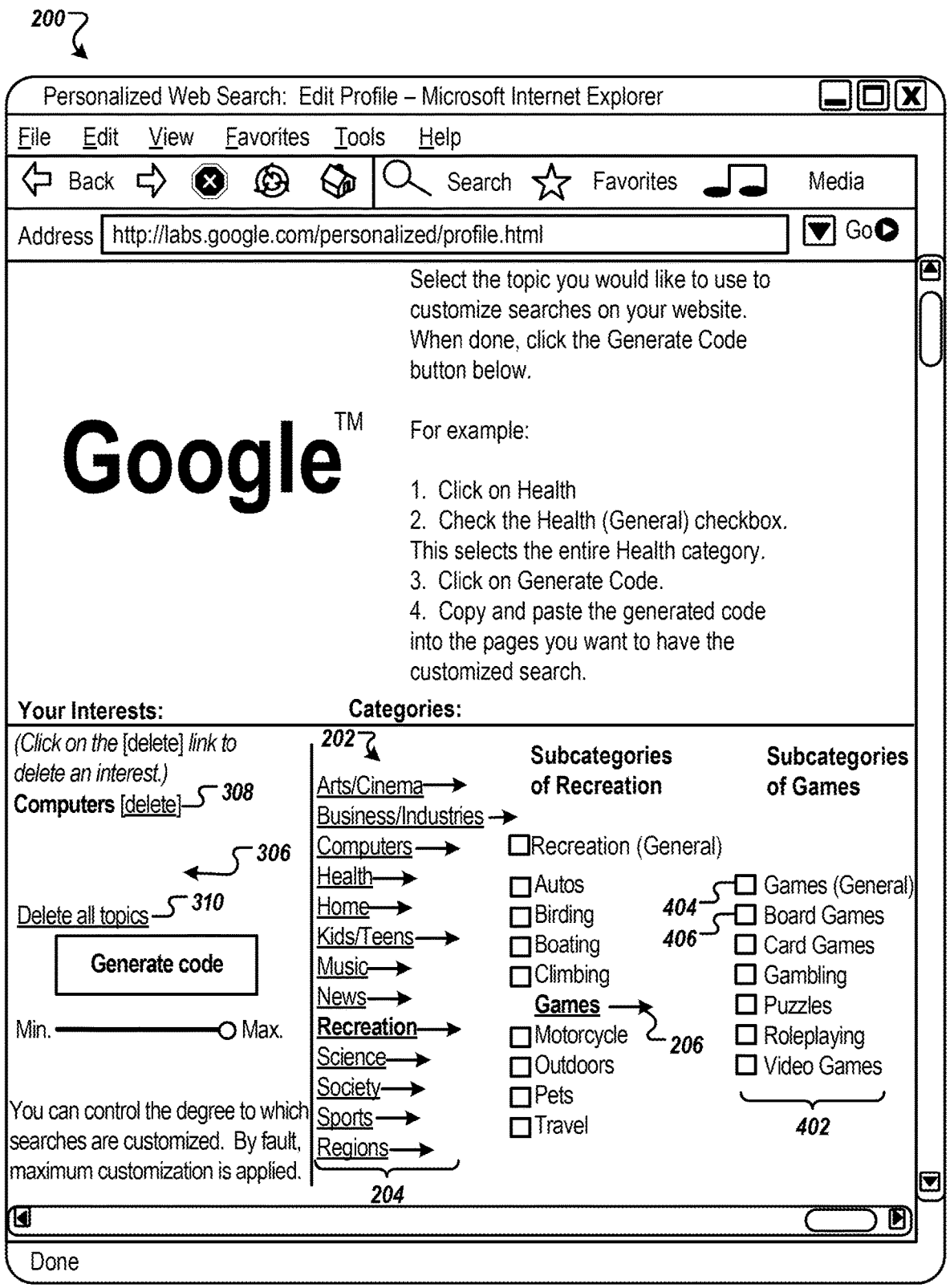
FIG. 4 further illustrates various subtopics of the topical directory.

The subtopics themselves can have any number of additional levels of subtopics. For example, FIG. 4 illustrates that the subtopic "Games" has further subtopics 402, "Board Games," "Card Games," etc. These were presented to the site operator in response to the site operator clicking on the subtopic arrow 206 next to the "Games" topic label. Again, the site operator can select either the entire subcategory by selecting checkbox 404, or any of the individual subtopic checkboxes 406. In one embodiment, in addition to the top level topics 204, there are two subtopic levels. This provides sufficient breadth and granularity of topical coverage, without imposing unnecessary computational complexity.

Referring again to FIG. 3, the site operator has indicated his interest in the "computers" topic generally. Clicking on the Generate Code button 208 causes the generation of a HTML code segment that the site operator can insert into one or more pages of the third party website. This code segment defines the search query interface 102, and contains parameters (here topic IDs) that describe the site profile defined by the site operator. An example of such a code segment is as follows:

```
<!-- Customized Search Query Interface-->
<FORM method=GET action=http://labs.google.com/per-
sonalized/search>
<A HREF=http://labs.google.com/personalized>
<INPUT TYPE=text name=q size=40 maxlength=255
value=''>
<INPUT TYPE=hidden name=site_profile value=127,126,
61,45,5>
<INPUT type=submit name=sa VALUE='Customized
Search'>
</FORM>
<!-- Customized Search Query Interface -->
```

Of interest here is line 5, which includes the variable site_profile as a set of integer topic IDs {127,126,61,45,5}, which are passed to the general search engine when the query is submitted. The general search engine maps the topic IDs to specific topics in the topical directory, to determine an associated boost value for documents that come from websites associated with the topic. In this example code segment, there are five topic IDs, but any number of IDs may be encoded here, depending on the number of topics that the site operator selects from the topical directory. The site operator adds the appropriate code segment to the desired webpages of the third party website, and publishes those pages for users to access.

In an alterative embodiment, the site operator's site profile is stored locally to the general search engine, for example in a site profile database. In this embodiment, the query interface simply returns a site_ID value instead of the list of topic IDs in site_profile. The general search engine then maps the site_ID value to the site operator's site profile in the database.

In one embodiment, the site operator can (optionally) specify a degree of influence by which the search results will be customized by the general search engine using the site profile. The input may be textual, such as value from 0 to 10 (which is then scaled an appropriate weighting scale) or graphical (e.g., using a slider type graphical control along an graphical axis; the position of the slider relative to the start and end points of the axis is then scaled to a weight). The customization control 309 allows the site operator to adjust the ranking of the individual documents/pages of the search results with respect to his interests, preferably as expressed in the customization profile. The customization control may be explained as controlling a degree of influence or contribution of the site operator's site profile to the ranking of the search results, and more specifically, scaling the boost that is applied to documents from websites associated with topics in the site profile.

FIG. 3 illustrates an example of a graphical customization control in an embodiment where it is a slider type control that includes a control handle 313 that is moved along a linear dimension between a minimum 312 to a maximum value 314. This type of control 309 is generally very intuitive and easy for site operators to understand how it operates. Alternative embodiments include dial type controls, similarly providing a variable adjustment between a minimum and maximum value, and radio buttons each with an associated predetermined adjustment amount (e.g., five radio buttons, associated respectively with 0%, 20%, 40%, 80%, and 100%). Those of skill in the art of site operator interface design will appreciate that other types of controls may be implemented to achieve essentially the same effect.

Another embodiment does not require the site operator to specify topical interests directly. Rather, the topics are automatically (e.g., programmatically) derived from attributes of one or more pages of the third party website or interactions by users of the site. The selected pages can be just the page(s) on which the search query interface appears, or all pages of the website, or some other set of pages. Various different types of attributes can be used to construct the site profile.

First, textual attributes, such as keywords, may be automatically associated with one or more pages of the site operator' website, based on frequency of appearance in the document and the general corpus, appearance (e.g., words in headings, boldface, etc., indicating relevant topics), or based on other statistical, morphological, syntactic, or grammatical features. The keywords are then mapped to previously identified topics in the topical directory, and the matching topics are included in the site profile. The mapping is easily done, for example, by providing a list of matching terms for each topic. An alternative approach is simply to scan the selected website pages for any of the topic terms themselves, and use the N (e.g., 10) most frequently appearing topic terms as the topics for the site profile. The automatic derivation of keywords for describing documents (e.g. websites and webpages) is well known to those of skill in the art, and thus not further explained here. Any known or later developed algorithm that generates one or more keywords (or topics) from a given input of pages may be used, and the particular technique employed for this purpose is not a material aspect of the invention.

Second, structural attributes of the selected pages may analyzed, in particular the outbound and/or inbound link structure. The inbound links to, and the outbound link from of a page, including the anchor text and the outbound URL of each link, are useful indicators of what a given page is about. Accordingly, the anchor text terms of inbound and/or outbound links may be used to derive topical keywords, and the domains of the linked pages may also be used by weighting any search results pages from these linked domains to improve their ranking in the final search results.

In another embodiment, the site profile of a site operator includes a list of the most relevant domains related to the site operator's website. For example, the site operator may provide a list of M (e.g., 5) domains that it deems of most relevant to user of the third party website. Documents from these websites will have their relevance scores weighted by the boost values associated with these websites, and thereby improve the ranking of any document in the search results which is from one of these sites.

Third, interaction attributes of users of the third party website may also be used for determining a site profile. Interaction attributes includes searches conducted by users and browsing patterns. For prior searches, the site operator or the general search engine can keep track of some number of prior searches by users at the third party website. The search query terms themselves can be analyzed, and some subset of them (e.g., the most frequently occurring query terms), can be used as the topic terms themselves, mapped onto the topic terms, or scanned for topic terms, as described above, to obtain the site profile topic IDs.

Interaction attributes also include the browsing patterns of site users. A user's site browsing patterns can be captured in a client side browser tool, such as a search query interface that is resident in the browser toolbar. For example, the browser tool can maintain a list of domains that a user accesses, including the order in which domains are accessed. In one embodiment, the domain information can be stored in domain tuples, as pairs of domains {origin_domain, destination_domain}, where the origin_domain is the site from which the user then links or access the destination_domain. From this domain access information, the relevant domains for any selected domain can be readily determined. First the domain access information from a plurality (e.g., hundreds or thousands, or more) users is obtained. For a given site operator's domain, all other domains that were either origin_domains or destination_domains can be determined. The most frequently occurring origin or destination domains are then considered the relevant domains for the site profile. In another embodiment, the general search engine site maintains for each of the third party sites that use its services, a list of the domains that are accessed by those users who also access the third party site, as well as the frequency of those visits to such domains.

Figure 5:
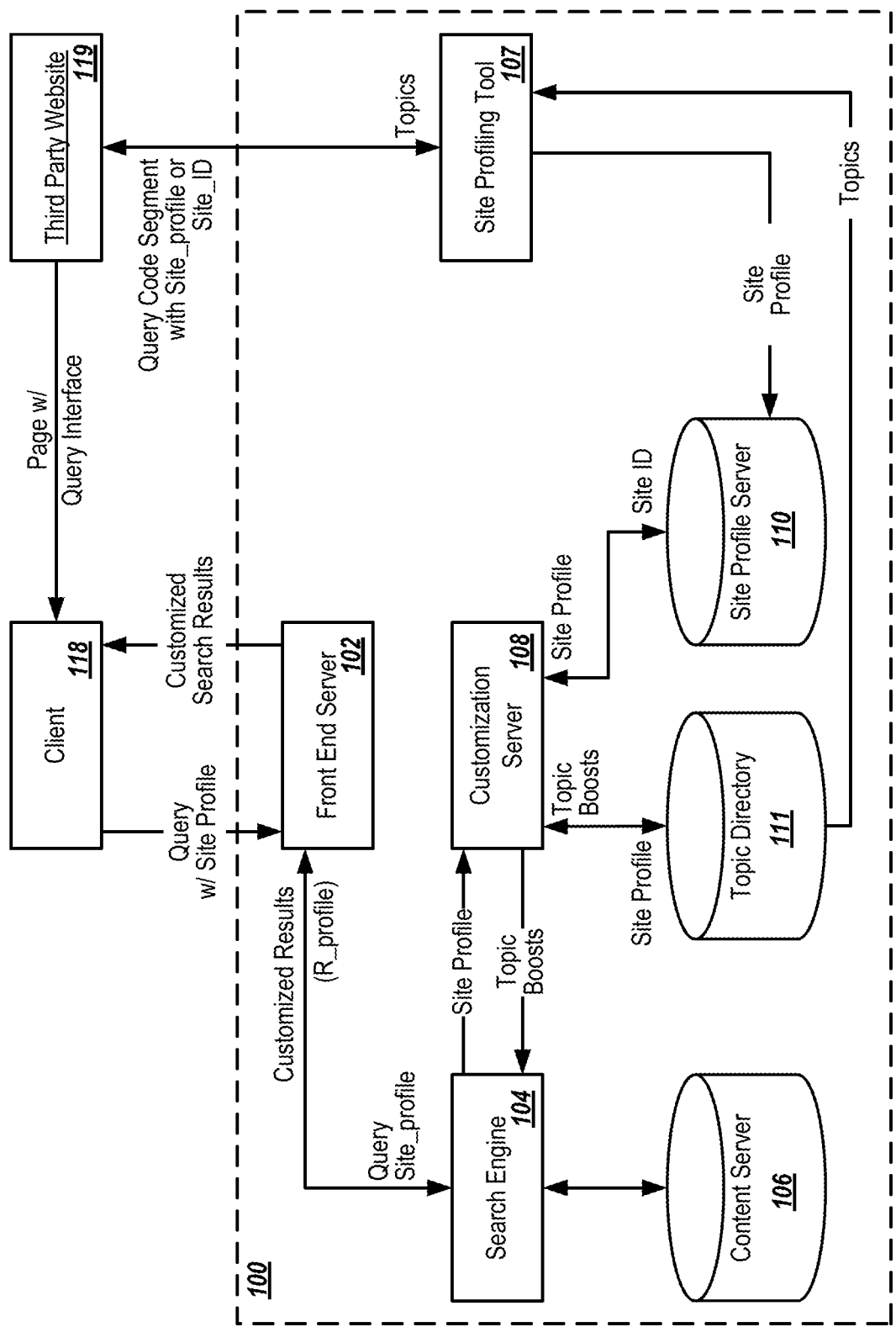
FIG. 5 illustrates a software architecture and associated dataflow for one embodiment.

In one embodiment, the customization of search results is provided by the following methodology and system. Those of skill in the art of search engine design can readily understanding the basic structure of a general search engine and its operation in which this methodology can be implemented. Referring now to FIG. 5, there is shown one embodiment of a software architecture and associated dataflow for practicing the present invention.

The user operates a client application 118, including a browser. The user accesses the site operator' website 119, enters a search query in the search query interface 102, as illustrated above. The search query (Q), along with the site profile parameters (e.g., site_profile topic IDs or site profile ID, depending on the implementation) is provided to the general search engine 104 via a front end server 102.

The front end server 102 issues a search request the general search engine 104 on the query Q and site profile. The front end server will receive back from the search engine 104 the customized search results, R_profile. The search engine 104 can apply any type of information retrieval scoring and relevance ranking process to determine an information retrieval score for each of a number of documents. The IR score can be determined, for example, using the PageRank algorithm, as disclosed in U.S. Pat. No. 6,285,999, "Method for node ranking in a linked database", which is incorporated by reference herein in its entirety and for all of its teachings.

The customized query (Q, site profile) contains the site operator's topic IDs (or site ID again, depending on the embodiment). The general search engine 104 follows a similar processing control flow as any normal query that is otherwise receives, but it accesses a customization server 108 during the scoring function by providing the site profile (or site ID) to the customization server 108.

The customization server 108 "boosts" documents that are relevant to the site profile for the site operator. If the customization server 108 receives the site profile directly, then it can determine the appropriate topic boosts for each topic identified in the site profile. If the customization server 108 receives a site ID of the third party website 119, then it can lookup the site profile in the site profile database 110. A site profiling tool 107 can be used to either generate the code segment as described above, or to generate the site profile directly using any of the various automated site analysis methods described above.

In one embodiment of the invention, the topic boosts are implemented using a set of maps (one map for each topic/subtopic in the directory), of the form:

{Site -->boost}

So for example, the category "Health" has a topic map of the form

{Site -->boost} which contains entries such as:

nih.gov -->5.8
cdc.gov -->7.9
med.stanford.edu -->3.5 where nih.gov, cdc.gov, and med.Stanford.edu are various sites (domains) that have been determined (either manually or automatically) to be related to the topic "Health." In other words, for each topic in the directory, there is a set of sites that have been determined to be relevant to the topic, and for each of these sites, a boost value is defined.

The boost for the sites listed in the topical directory is generally determined as follows:

a) A "site graph" is generated where nodes of the graph are sites (basically, pages on the same host) and edges between nodes are weighted based on the number of pages from one site that link to pages on another. This same type of graph can be used to compute all topic boost maps.

b) For each topic in the directory, say "Health", a number of sites are selected as "start sites" S0 whose home page is listed in the Open Directory. For example, for a university like Stanford, start sites may be selected as any site ending in .stanford.edu.

c) A computation is run in two passes:
  i) first identify a set of sites S1 that are linked-to heavily by those sites in S0, with each site in S1 assigned a weight according to how heavily it's linked-to by sites in S0.
  ii) then identify those sites S2 that are linked-to heavily by those sites in S1, weighted as with S1.

d) The sites in S2 are boosted with their assigned weights.

When a customized query comes in with a site profile (e.g., {Health, Music}), then the customization server 108 consults the respective maps for these topics. When a document in the query results is from a domain included a topic map, the customization server 108 boosts the IR score for the document by the boost value associated with topic, so that the document gets its IR score improved.

In the embodiment described above where the site operator directly specifies a number of most relevant sites, again the customization server 108 can obtain the corresponding boost value for each of these sites from the topic maps.

For example if http://www.med.stanford.edu/research/ were one of the results for query Q, and site profile included "Health," then that result would get a multiplicative boost of 3.5 to its IR score, because that page is on the site med-.stanford.edu, which as illustrated above has a boost value of 3.5. For multiple interests, the values in the corresponding maps are multiplied together for a combined effect. Further details of one implementation for determining the boost for sites in the directory boost map is described in the related application, "Improved Methods for Ranking Nodes in Large Directed Graphs," which is incorporated by reference.

The front end server 102 receives the customized search results R_profile, and passes them back the client application 118 for display to the user.

In an embodiment in which the site operator is provided with, and uses the customization control 309, the following additional steps are undertaken.

First, the front end server 102 makes two search requests to the search engine 104, the customized query R_profile, as above, and another request, a base query, just on the query Q with the site profile being set to NULL. The base query (Q, NULL) is the same as searching for Q on the search engine 104 without any profile information, so R_base is the result set that the general search engine 104 would normally return in response to the query. This search corresponds to the degree of influence being 0%, e.g., the customization slider 309 set at its minimum position 312. R_profile represents the degree of influence of the site profile being maximal (i.e., 100%), for example, where the slider is at its maximum position 314. In one embodiment, the control 309 has 11 positions (positions 0 through 10), but any number of positions may be used, and the rankings for intermediate positions between 0 and 10 are linearly interpolated; this means using R_base and R_profile, the customization server 108 can determine the appropriate ranking of the documents.

The customization server 108 appends the results in R_profile that are not in R_base to R_base to get a list of all unique results (either in R_base or R_profile) called R_all. The customization server 108 then assigns consecutive identification numbers to the results in R_all that serve as identifiers (R_IDs). For each of these result documents then, the customization server 108 boosts (e.g., multiplies) each document's R score by the boost value from the topic directory (if any) of its domain, and the interpolated weighting factor for the site operator's specified degree of influence (e.g. 0.5, when the customization control 309 is set halfway between the maximum and minimum values).

The present invention has been described in particular detail with respect to one possible embodiment. Those of skill in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component.

Some portions of above description present the features of the present invention in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "calculating" or "determining" or "identifying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

The present invention also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, or any type of media suitable for storing electronic instructions, and each coupled to a computer system bus. Those of skill in the art of integrated circuit design and video codecs appreciate that the invention can be readily fabricated in various types of integrated circuits based on the above functional and structural descriptions, including application specific integrated circuits (ASIC). In addition, the present invention may be incorporated into various types of video coding devices.

The algorithms and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present invention is not described with reference to any particular programming language. It is appreciated that a variety of programming languages may be used to implement the teachings of the present invention as described herein, and any references to specific languages are provided for disclosure of enablement and best mode of the present invention.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

What is claimed is:

1. A method performed by one or more computers of a server system, the method comprising:
    receiving, by the one or more computers, a request from a client device over a communication network, the request submitted through a search interface of a web resource hosted at an Internet domain that is different from an Internet domain of a search engine;
    identifying, by the one or more computers by use of the search engine, content items responsive to the request;
    identifying, by the one or more computers and for each of the content items, an Internet domain used to specify a location to access the content item on the Internet;
    generating, by the one or more computers, a response to the request that prioritizes the content items based at least in part on the Internet domains identified for the content items according to the Internet domain through which the search interface of the web resource is hosted; and
    providing, by the one or more computers, the generated response to the client device over the communication network.

2. The method of claim 1, wherein the request comprises a search query;
    wherein the content items comprise documents responsive to the search query;
    wherein identifying the Internet domain for each of the content items comprises determining, for each of the documents, an Internet domain that is part of a universal resource locator (URL) for the document; and wherein generating the response comprises generating a resource that includes search results corresponding to the documents, wherein the search results are ranked at least in part based on the respective Internet domains for the documents.

3. The method of claim 1, further comprising ranking the content items based at least in part on the Internet domains for the content items; and wherein generating the response comprises generating a response that indicates the ranking of the content items.

4. The method of claim 3, wherein generating a response that indicates the ranking of the content items comprises generating a document in which information corresponding to the content items is displayed in an order corresponding to the ranking.

5. The method of claim 1, wherein the content items include a first content item associated with a first Internet domain, and a second content item associated with a second Internet domain, the second Internet domain being different from the first Internet domain; and wherein generating the response comprises generating a response configured to display a first content item of the content items before a second content item of the content items based at least in part on the first Internet domain or the second Internet domain.

6. The method of claim 1, wherein generating the response to the request comprises generating a document that has displayable content organized based at least in part on the Internet domains for the content items.

7. The method of claim 1, further comprising:
determining a score for each of the content items;
adjusting the scores for one or more of the content items based on the Internet domains identified for the one or more of the content items;
wherein generating the response comprises generating a response prioritizing the content items based on the adjusted scores.

8. The method of claim 1, wherein generating the response comprises:
determining, for at least one content item of the content items, that the Internet domain identified for the at least one content item matches a predetermined Internet domain; and
in response to determining that the Internet domain identified for the at least one content item matches a predetermined Internet domain, adjusting a score for the at least one content item that affects a ranking of the at least one content item among the other content items.

9. The method of claim 1, wherein identifying the Internet domain for a content item comprises identifying a URL for the content item.

10. The method of claim 1, further comprising determining a source of the request; and wherein generating the response comprises generating the response to further prioritize the content items based on the source of the request.

11. The method of claim 10, wherein the request comprises a search query submitted using a web page, and wherein the source of the request comprises an identifier for the web page used to submit the search query.

12. The method of claim 1, wherein the content items comprise at least one of a web page, image data, audio data, or video data.

13. The method of claim 1, wherein identifying the Internet domains for the content items comprises, for each of the content items:
identifying a URL for the content item; and
identifying the Internet domain for the content item from the URL of the content item.

14. A system comprising:
a computer including a processor and a memory device storing instructions that, when executed by the computer, causes the computer to perform operations comprising:
receiving, by the computer, a request from a client device over a communication network, the request submitted through a search interface of a web resource hosted at an Internet domain that is different from an Internet domain of a search engine;
identifying, by the computer by use of the search engine, content items responsive to the request;
identifying, by the computer and for each of the content items, an Internet domain used to specify a location to access the content item on the Internet;
generating, by the computer, a response to the request that prioritizes the content items based at least in part on the Internet domains identified for the content items according to the Internet domain through which the search interface of the web resource is hosted; and
providing, by the computer, the generated response to the client device over the communication network.

15. The system of claim 14, wherein the request comprises a search query;
wherein the content items comprise documents responsive to the search query;
wherein identifying the Internet domain of each of the content items comprises determining, for each of the documents, an Internet domain associated with the document; and
wherein generating the response comprises generating a resource that includes search results for the documents ranked at least in part based on the Internet domains associated with the documents.

16. The system of claim 14, wherein the operations comprise ranking the content items based at least in part on the Internet domains for the content items; and
wherein generating the response comprises generating a response that indicates the ranking of the content items.

17. The system of claim 16, wherein generating a response that indicates the ranking of the content items comprises generating a document in which information corresponding to the content items is displayed in an order corresponding to the ranking.

18. The system of claim 14, wherein the content items include a first content item associated with a first Internet domain, and a second content item associated with a second Internet domain, the second Internet domain being different from the first Internet domain; and
wherein generating the response comprises generating a response configured to display a first content item of the content items before a second content item of the content items based at least in part on the first Internet domain or the second Internet domain.

19. The system of claim 14, wherein identifying the Internet domain for a content item comprises identifying a URL for the content item.

20. One or more non-transitory computer-readable media storing instructions that, when executed by one or more computers, cause the one or more computers to perform operations comprising:
- receiving, by the one or more computers, a request from a client device over a communication network, the request submitted through a search interface of a web resource hosted at an Internet domain that is different from an Internet domain of a search engine;
- identifying, by the one or more computers by use of the search engine, content items responsive to the request;
- identifying, by the one or more computers and for each of the content items, an Internet domain used to specify a location to access the content item on the Internet;
- generating, by the one or more computers, a response to the request that prioritizes the content items based at least in part on the Internet domains identified for the content items according to the Internet domain through which the search interface of the web resource is hosted; and
- providing, by the one or more computers, the generated response to the client device over the communication network.

* * * * *